United States Patent
Shaker

(10) Patent No.: US 9,242,116 B2
(45) Date of Patent: Jan. 26, 2016

(54) METHOD OF MAKING AN AUTOMATED EXTERNAL DEFIBRILLATOR

(71) Applicant: Matthew Robert Shaker, Centreville, VA (US)

(72) Inventor: Matthew Robert Shaker, Centreville, VA (US)

( * ) Notice: Subject to any disclaimer, the term of this patent is extended or adjusted under 35 U.S.C. 154(b) by 462 days.

(21) Appl. No.: 13/871,504

(22) Filed: Apr. 26, 2013

(65) Prior Publication Data

US 2014/0317914 A1    Oct. 30, 2014

(51) Int. Cl.
*H01R 43/00*    (2006.01)
*A61N 1/39*    (2006.01)
*A61N 1/04*    (2006.01)

(52) U.S. Cl.
CPC .............. *A61N 1/3993* (2013.01); *A61N 1/046* (2013.01); *A61N 1/3968* (2013.01); *Y10T 29/49002* (2015.01); *Y10T 29/49117* (2015.01)

(58) Field of Classification Search
CPC ... A61N 1/3993; A61N 1/3968; A61N 1/046; A61N 1/39; A61N 1/3987; Y10T 29/49117; Y10T 29/49124; Y10T 29/49002
USPC ....................... 29/825, 829, 592.1; 607/4, 5, 1
See application file for complete search history.

(56) References Cited

U.S. PATENT DOCUMENTS

| 2007/0032830 A1* | 2/2007 | Bowers ..................... A61N 1/39 607/5 |
| 2009/0240297 A1* | 9/2009 | Shavit ....................... A61N 1/39 607/5 |
| 2010/0241181 A1* | 9/2010 | Savage ................... A61N 1/046 607/5 |
| 2011/0046688 A1* | 2/2011 | Schwibner ............... A61N 1/39 607/5 |
| 2013/0066390 A1* | 3/2013 | Schwibner ........... A61N 1/3968 607/7 |
| 2014/0277227 A1* | 9/2014 | Peterson .............. A61N 1/3993 607/7 |

OTHER PUBLICATIONS

Science Spin, Issue 44, Jan.-Feb. 2011.*

* cited by examiner

*Primary Examiner* — Peter DungBa Vo
*Assistant Examiner* — Azm Parvez
(74) *Attorney, Agent, or Firm* — Louis Ventre, Jr.

(57) ABSTRACT

A method includes making a device capable of administering an electrical shock to a patient and operable with a smartphone. The steps include providing a case; providing an automated external defibrillator fitting within the case; providing a case input/output port to the automated external defibrillator that mates with a corresponding smartphone input/output port; and providing foldable pads fitting within the case. Each foldable pad has electrodes that are electrically connectable to the automated external defibrillator. Each foldable pad is unfolded to expose a surface of each electrode to be placed in contact with the skin of the patient. Additional steps may include providing on non-volatile memory a combined operating system for both a smartphone and the automated external defibrillator such that the combined operating system auto loads upon starting the device after connection of the smartphone to the case input/output port.

3 Claims, 4 Drawing Sheets

METHOD OF MAKING AN AUTOMATED EXTERNAL DEFIBRILLATOR

TECHNICAL FIELD

In the field of light, thermal, and electrical application, a method of making a device for applying electricity to the surface of the body near the heart using electrodes to stimulate or restore normal or quasi-normal operation of the heart.

BACKGROUND ART

Portable medical devices for electrically stimulating the heart are commonly known as automated external defibrillators (AED's). These devices are typically housed in a briefcase-sized container. They are frequently mounted on the wall or in a kiosk for use in emergencies. The present invention teaches the manufacture of a miniature AED operable in combination with a smartphone. The method taught herein produces an AED that is a little larger than a cellular telephone, but when combined with a smartphone is capable of full function to diagnose and correct arrhythmia of the heart by delivering electric shocks while interacting with emergency service providers.

AEDs are designed to be used by laypersons in the event of a person suffering from life threatening cardiac arrhythmias, which often lead to cardiac arrest. More and more public access places are now being equipped with AEDs. Examples include airplanes, restaurants, business and government offices, shopping centers, schools and fitness centers.

A typical AED case will include a software operating system, sensors to detect the patient's condition, a battery and associated components to store electrical energy, and electrodes or pads for placement on the patient's skin near the heart. The "A" in AED stands for "Automatic," which describes the software's ability to autonomously analyze a patient's condition once the electrodes are in place on the patient's body. Most AEDs include voice prompts as well as visual displays to guide the person delivering the electrical shock.

When turned on, the typical AED software operating system will instruct the user to attach the electrodes (contained within sticky pads) to the patient. The pads adhere to the skin and allow the AED to sense the electrical output from the heart and determine if the patient's heart is in a state where an electrical shock will help, to wit, that the heart rhythm is either in ventricular fibrillation or ventricular tachycardia. If the device determines that a shock would help, then the AED software system enables the battery to charge one or more internal capacitors in preparation to deliver the electrical shock.

SUMMARY OF INVENTION

A method of making a device commonly known as an automated external defibrillator made operable with a smartphone. When combined with a smartphone, the device is capable of administering an electrical shock to a patient suffering from arrhythmia of the heart. Steps include providing a case; providing an automated external defibrillator fitting within the case; providing an input/output port on the automated external defibrillator that mates with a corresponding input/output port on the smartphone; providing foldable pads fitting within the case, wherein each of the foldable pads comprises electrodes that are electrically connectable to and detachable from the automated external defibrillator, wherein each of the foldable pads may be unfolded to expose a surface of each electrode so that these surfaces may be placed in contact with the skin of the patient; optionally providing a combined operating system for both a smartphone and the automated external defibrillator, which auto loads and replaces the smartphone operating system after connecting the smartphone to the case input/output port and after starting the device; optionally providing non-volatile memory connectable to the smartphone; and adding the combined operating system to the non-volatile memory.

Technical Problem

Present generation AEDs are relatively large, the smaller of these being the size of a large attaché case. Others can be heavy and are bulky, preventing individuals from owning and routinely carrying such devices. Present generation AEDs are of a size and shape that they impede portability, such that they are usually located in a fixed place by a facility owner, similar to distribution of wall-mounted fire extinguishers in a building. Such limited availability can impede ready access in a time of emergency. Current AEDs do not offer interconnectivity with a smartphone, which are ubiquitous in today's society.

Solution to Problem

The solution is a method of making an AED where some of the functions are moved to an attachable smartphone. Smartphones contain capabilities that would be useful in reducing the size, weight, portability and cost of the AED, while at the same time expanding the communication and interactivity capabilities of the AED. The method makes an AED that permits interconnection with a user-provided smartphone to leverage smartphone technology.

Advantageous Effects of Invention

The method of making an AED can result in a miniature AED that might be routinely carried and used anywhere, by potential users. Additionally such an AED could employ the smartphone to automatically relay the location of the patient while wirelessly telephoning for help and allowing ready interaction with emergency services.

BRIEF DESCRIPTION OF DRAWINGS

The drawings illustrate preferred embodiments of the method of the invention and the reference numbers in the drawings are used consistently throughout. New reference numbers in FIG. 2 are given the 200 series numbers. Similarly, new reference numbers in each succeeding drawing are given a corresponding series number beginning with the figure number.

DESCRIPTION OF EMBODIMENTS

In the following description, reference is made to the accompanying drawings, which form a part hereof and which illustrate several embodiments of the present invention. The drawings and the preferred embodiments of the invention are presented with the understanding that the present invention is susceptible of embodiments in many different forms and, therefore, other embodiments may be utilized and structural, and operational changes may be made, without departing from the scope of the present invention. For example, the steps in the method of the invention may be performed in any order that results making the automated external defibrillator.

Figure 1:
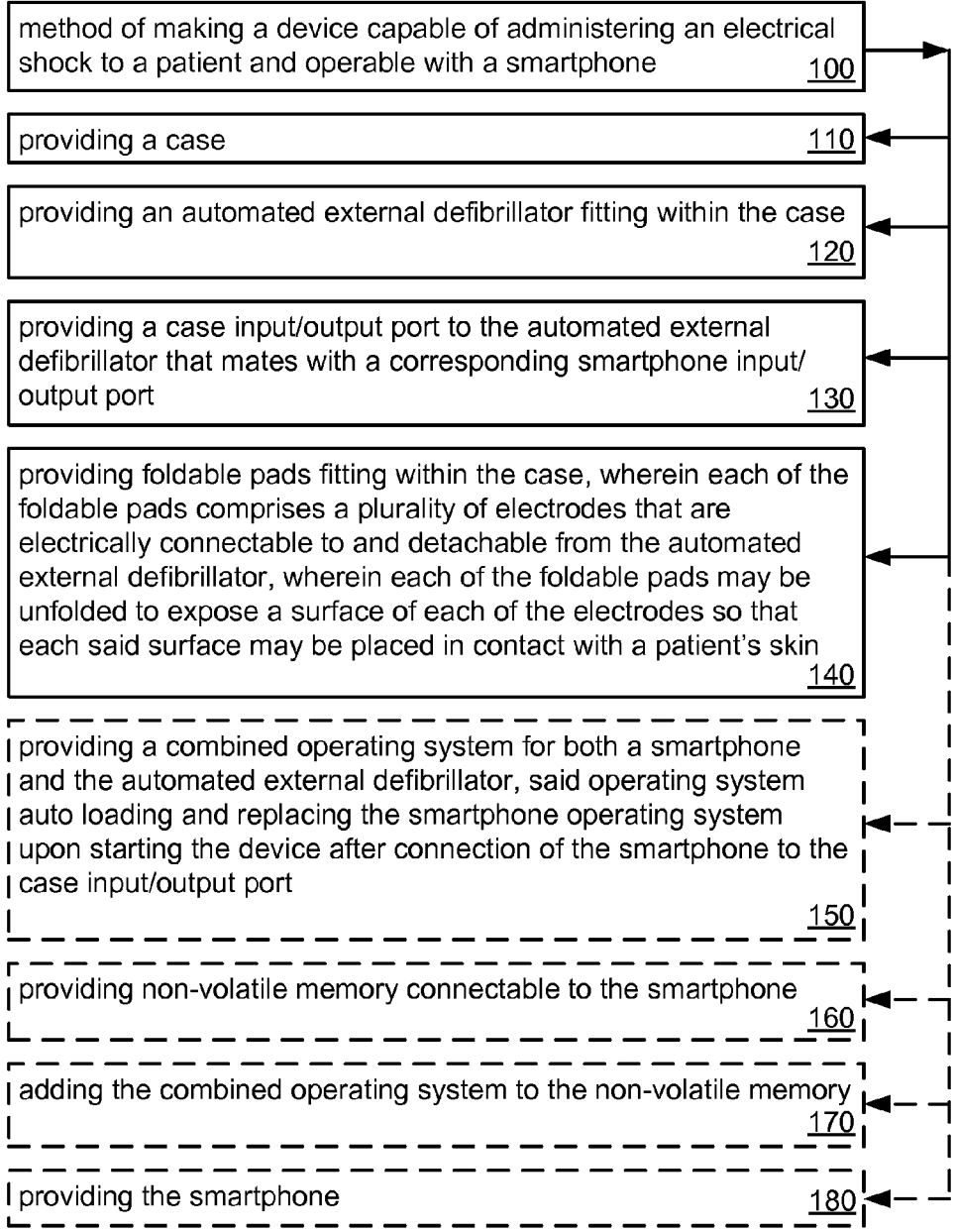
FIG. 1 is a block diagram of illustrating the method of making an automated external defibrillator operable in combination with a smartphone.

FIG. 1 shows the steps in the method. The dashed blocks and lines of FIG. 1 indicate preferred but optional steps. The first block (100) at the top of FIG. 1 indicates that what is disclosed is a method of making a device (200) capable of administering an electrical shock to a patient and operable with a smartphone (240). The device (200) capable of administering an electrical shock to a patient is typically referred to as an automated external defibrillator (AED), but for purposes of explaining the invention, the AED comprises the components needed to generate the electrical shock, which are made operable by their combination with a smartphone (240).

As used herein, the smartphone (240) is a mobile phone with a Global Positioning System (GPS) chip, a screen capable of full motion video, a speaker phone, non-transitory computer memory and one or more computer processors. The smartphone (240) may also be a personal digital assistant, or a tablet computer. Preferably, a smartphone is a communication computer that combines the functions of a personal digital assistant (PDA) with a cell phone. Many smartphones include the functionality of portable media players, compact digital cameras, pocket video cameras, and GPS navigation units to form one multi-use device. Modern smartphones also include high-resolution touch screens and web browsers that display Internet web pages. Typically, high-speed data access in a smartphone is provided by Wi-Fi and mobile broadband.

The smartphone (240) is preferably attached to the case input/output port (210) via the data connection for the smartphone (240), that is, the smartphone input/output port (250). While a smartphone (240) will have its own battery, preferably, the case (205) also powers the smartphone (240) using the AED built-in battery or batteries (310). This option could be considered a "rescue mode" for the smartphone (240), since the device (200) would provide supplemental power to the smartphone (240) in the event the battery on the smartphone (240) had an insufficient charge. The case (205) preferably includes an electrical cord (220) to plug into a standard electrical outlet. The electrical cord (220) is a standard power cord and is preferably combined with an AC/DC adapter either within the case (205) or on the end of the electrical cord (220). This will permit charging both the device (200) for use and the smartphone (240). This arrangement provides backup power for the smartphone (240).

Figure 2:
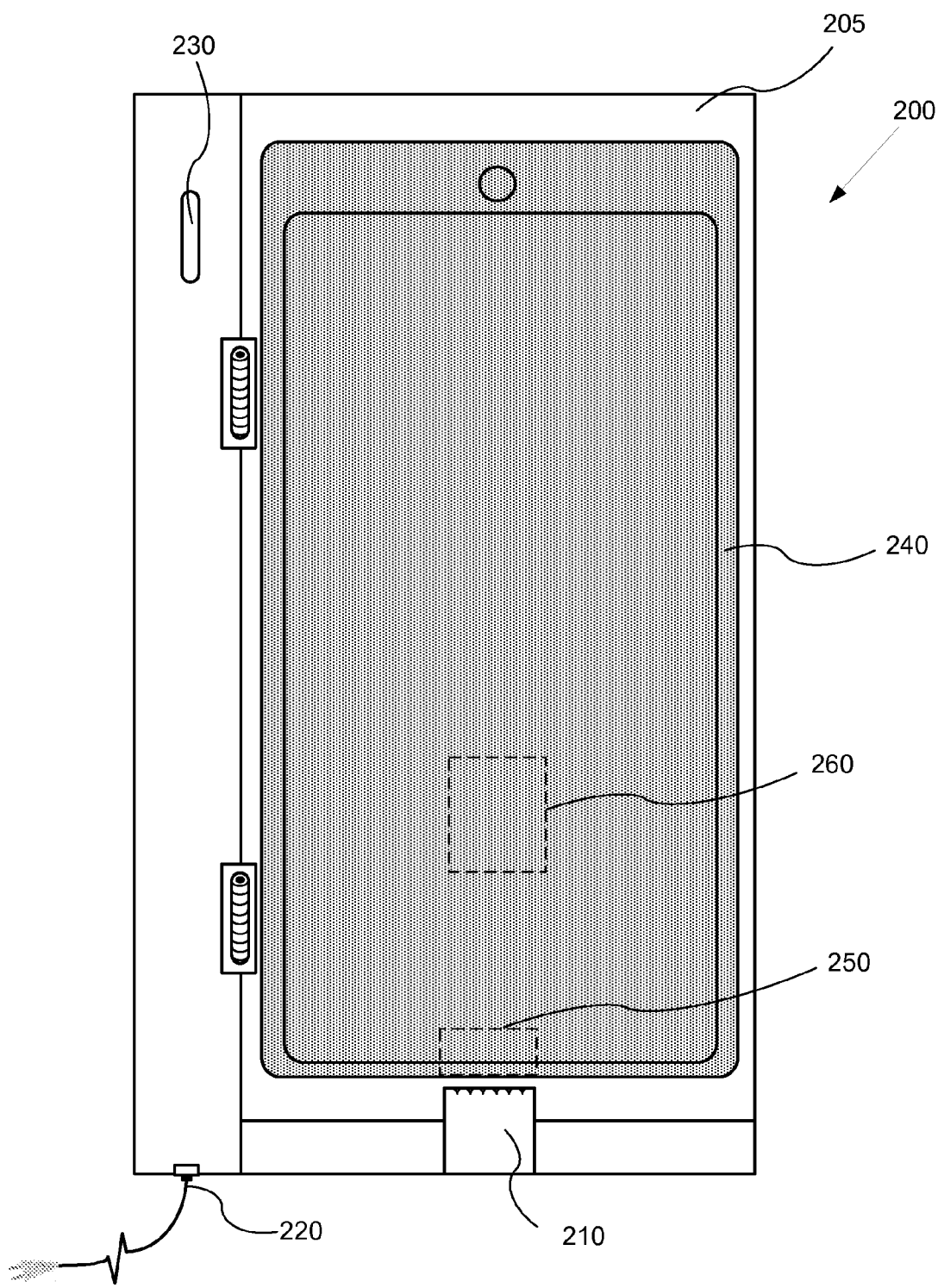
FIG. 2 is a plan view of a case in folded position showing the smartphone.

The second block (110) from the top of FIG. 1 shows that the method includes a step of providing a case (205). Preferably, the case is itself foldable so that it is only a little larger than a smartphone (240), which in this instance is a cell phone. The smartphone (240) is plugged into the case (205) on an external face of the closed case (205), as shown in FIG. 2. The case (205) holds the components of the automated external defibrillator (300).

Figure 3:
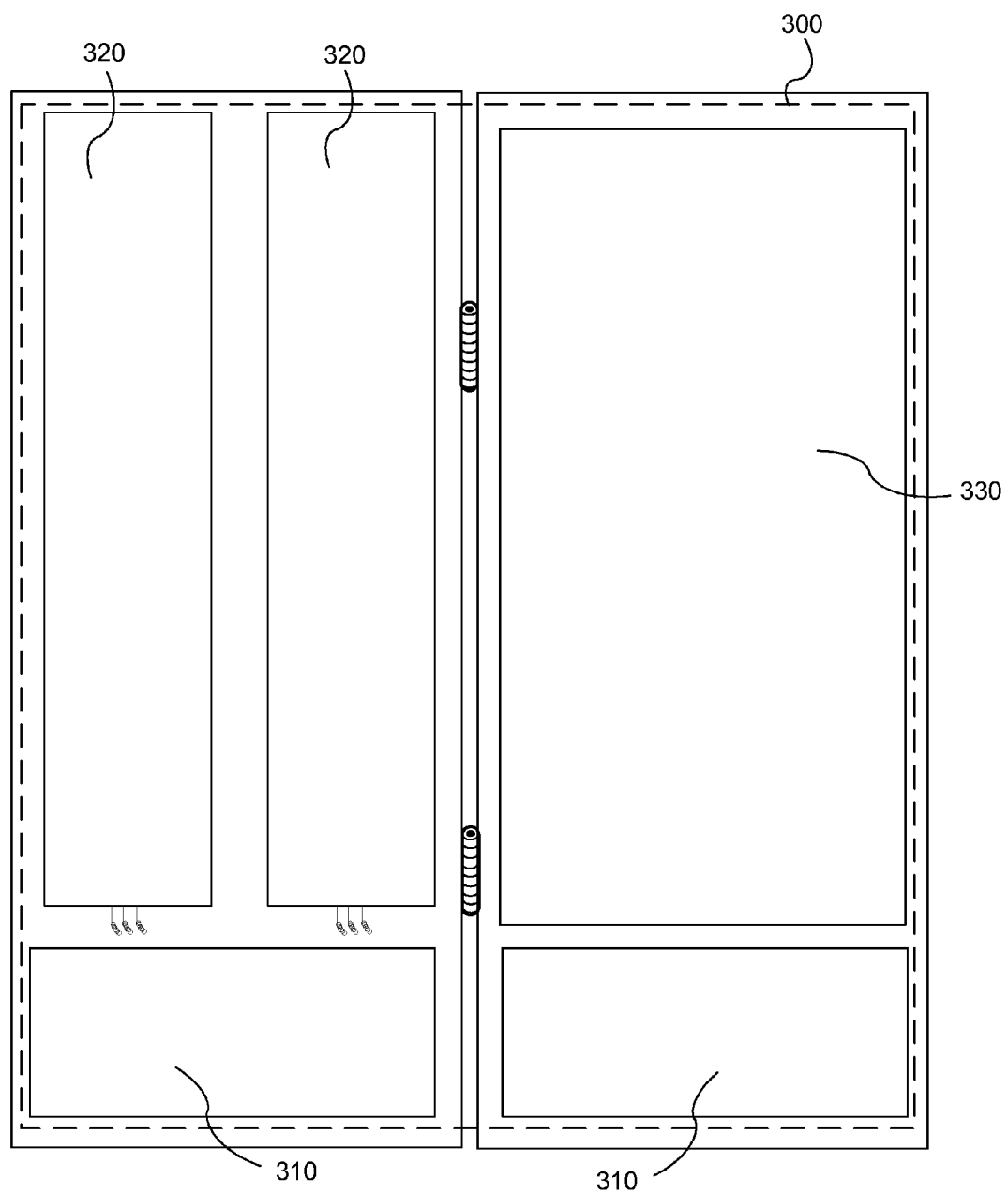
FIG. 3 is plan view of an opened case showing the automated external defibrillator with pads in the folded and stored position.

The third block (120) from the top of FIG. 1 shows that the method includes a step of providing an automated external defibrillator (300) fitting within the case (205). This step provides all of the components needed to create and deliver the electric shock. The essential components are well known, including one or more batteries (310), a capacitor (330) and the electrodes (410) within the foldable pads (320), shown folded and in a storage position in FIG. 3.

The automated external defibrillator (300) will also require electronics, hardware, and software to communicate with the smartphone and operate the automated external defibrillator (300). The AED operating system is preferably located on the non-volatile memory (260) together with the smartphone (240) operating system. Such non-volatile memory (260) may be within the case (205), on the smartphone (240) or shared between the AED and the smartphone (240). Location of the memory is a size, weight and operability issue that may be varied to optimize the device (200) design. Also, because different smartphones vary widely in size, memory card capacity, and form factors, the case (205) may be customized to suit the smartphone model. Thus, the internal placement of parts may vary accordingly.

The fourth block (130) from the top of FIG. 1 shows that the method includes a step of providing a case input/output port (210) to the automated external defibrillator (300) that mates with a corresponding smartphone input/output port (250). Such ports are common to most smartphones. In an alternative embodiment, the automated external defibrillator (300) will not function to deliver a shock without a smartphone (240) connected to the device (200). In that embodiment, the smartphone (240) provides the necessary software to enable device (200) operability. Also in that embodiment, there would be a step of providing an automated external defibrillator (300) fitting within the case, said automated external defibrillator being inoperative without the addition of a smartphone (240).

The fifth block (140) from the top of FIG. 1 shows that the method includes a step of providing foldable pads (320) fitting within the case (205), wherein each of the foldable pads (320) comprises a plurality of electrodes (410) that are electrically connectable to and detachable from the automated external defibrillator (300), wherein each of the foldable pads (320) may be unfolded to expose a surface (420) of the electrodes (410) so that each said surface (420) may be placed in contact with a patient's skin. Preferably, there are two foldable pads (320) and each of the foldable pads (320) will have sticky glue surrounding the surface (420) so that when unfolded each of the foldable pads (320) will stick to the skin of a patient, making good electrical contact between the skin and each electrode surface. In an alternative embodiment, there is only a single electrode within any of the foldable pads.

Figure 4:
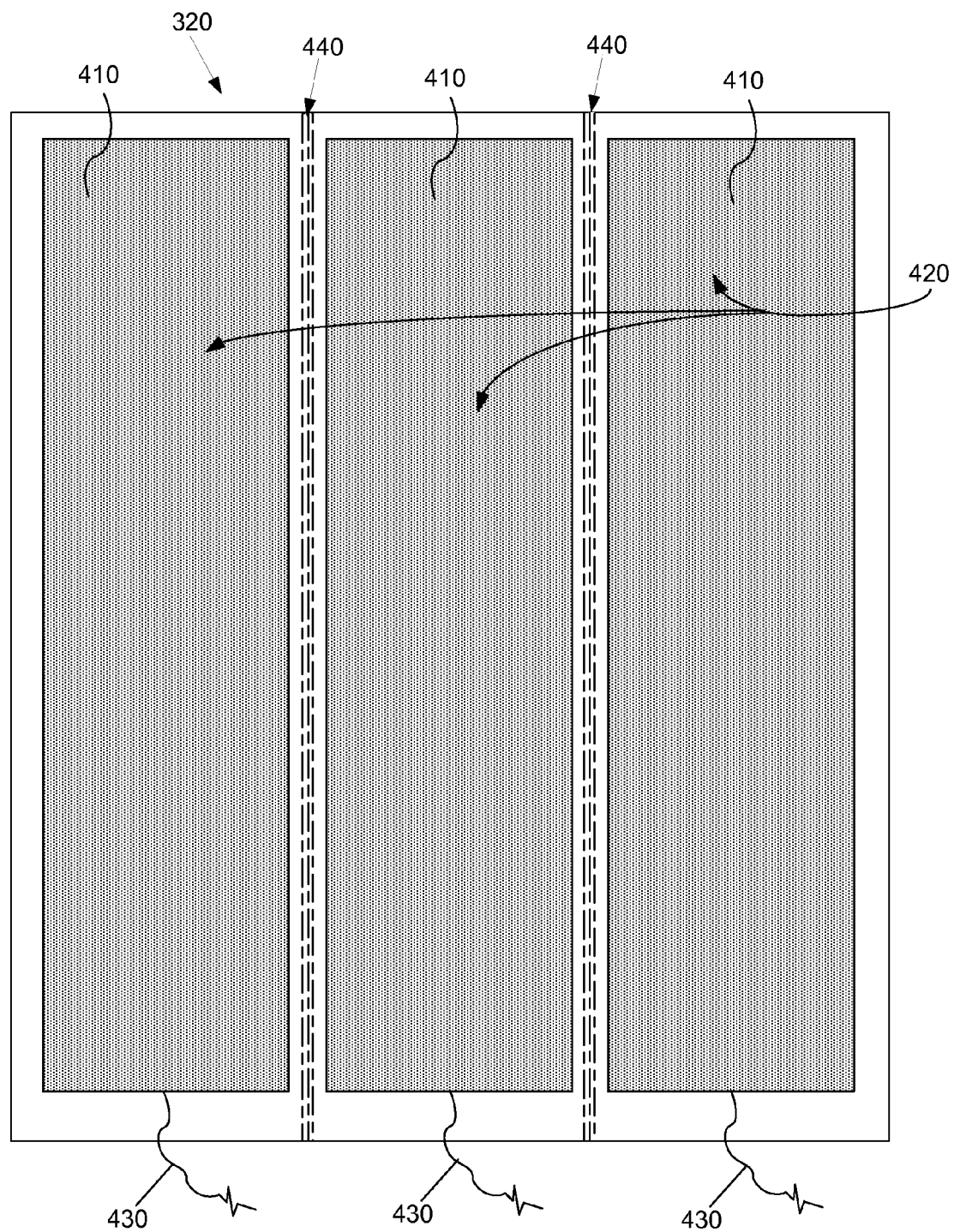
FIG. 4 is a plan view of an unfolded pad showing fold lines and three electrodes.

These foldable pads (320) and the electrodes (410) are preferably disposable. The foldable pads (320) may fold any number of times, depending on the size of the case (205). It is anticipated that the foldable pads (320) will be available with two or more electrodes (410) to provide an optimal surface area for a variety of smartphone sizes. For example, FIG. 4 illustrates a pad having two folds (440) and three electrodes (410). Thus, this foldable pads (320) embodiment folds into thirds. This single foldable pad contains 3 electrodes, each with its own electrical lead (430) so that each electrode actuates in parallel. The electrodes (410) preferably have peel-off adhesive covering that once removed, reveals a pre-glued and ready to stick surface surrounding the electrodes (410). A pad that folds in half would preferably have two electrodes (410) and each of these electrodes would have its own electrical lead. The electrodes (410) are sufficiently pliable such that they themselves may also be folded. A designated button on the smartphone (240) would preferably initiate the shock. Alternatively, a button (230) may be provided on the case (205) to manually initiate the shock.

The sixth block (150) from the top of FIG. 1 shows that the method optionally includes a step of providing a combined operating system for both a smartphone (240) and the automated external defibrillator (300), said operating system auto loading and replacing the smartphone operating system upon starting the device (200) after connection of the smartphone (240) to the case input/output port (210).

Preferably, the case (205) folds and locks closed in the approximate shape of the smartphone (240). Unlocking and unfolding the case (205), preferably, starts the device, that is, such action triggers auto loading of the combined operating system for operating both the automated external defibrillator (300) and the smartphone (240).

After the smartphone is linked to the case (205) by connecting it to the case input/output port (210), then, preferably, the device is automatically started or activated by opening the case (205). If the smartphone (240) is on when it is connected to the case, then preferably, the act of opening the case (205) automatically turns off the smartphone (240) and auto loads the combined operating system.

The need for a combined operating system is due to federal regulation of AEDs. While it is possible that the U.S. Food and Drug Administration (FDA) would approve using the smartphone on-board mobile operating system for the device (200), as an adjunct for its current regulations implementing international standard IEC 62304, this is a longer term implementation. In the absence of such FDA approval, the device (200) is preferably made operable by a regulatory-approved operating system to run the smartphone and the AED, thereby using the smartphone's computer platform but not its native software. This programming is preferably stored on an SD card (or micro SD card) for immediate use within the smartphone (240). The SD card may be within the case and accessed via the data port or used within the smartphone (240). If within the smartphone, a person would swap out the existing SD card in their smartphone (240) and the new SD card would enable smartphone (240) to automatically startup with the combined operating system when the smartphone (240) is connected to the case input/output port (210).

Since a typical smartphone (240) will contain one or more computer processors and computer memory, it is preferable that the combined operating system is run by the smartphone (240). As an example of one embodiment, the combined operating system will preferably perform steps, such as: instructing the user to unfold the foldable pads (320) and place them on the patient; assessing the patient's heart rhythm; determining if a shock is necessary; charging the capacitor; instructing the user to initiate the shock (push a button on the smartphone or the device); and running smartphone routines, like calling 911 and making GPS determinations, which may be done in parallel with the other steps. For this embodiment, the intent is to use the computing capability of the smartphone (240) to perform the work that otherwise might be done by a computer in the AED.

The seventh block (160) from the top of FIG. 1 shows that the method optionally includes a step of providing non-volatile memory (260) connectable to the smartphone (240). The non-volatile memory (260) is preferably in the form of an SD card.

The eighth block (170) from the top of FIG. 1 shows that the method optionally includes a step of adding the combined operating system to the non-volatile memory (260).

The ninth and bottom block (180) on FIG. 1 shows that the method optionally includes a step of providing the smartphone (240). Since this device is ideally small enough for people at risk to carry around with them, the smartphone (240) is preferably, user provided. This permits individuals to use their own equipment to make the device operable.

In operation, the smartphone's screen and speakers would be used to walk the first responder through the process of connecting the pads, waiting for the device to charge, instructing the first responder not to touch the patient and instructing the first responder to shock the patient. Unlike AEDs in the market today, full motion video could augment audio instructions.

Smartphones that have a Global Positioning System (GPS) will preferably record where the use if the device (200) occurred and automatically transmit this information to emergency personal via voice or text. Video/audio conferencing with 911 may also be offered where available.

EXAMPLE

Embodiment 1

This embodiment starts with foldable pads (320) each measuring approximately 4.75 inches by 5.5 inches. Each of the foldable pads (320) has two electrodes (410) and each of the electrodes (410) has a lead or electrical wire coming off the foldable pad to attach to the automated external defibrillator (300). Each of the electrodes (410) measures approximately 2 inches by 4 inches and is affixed to, or embedded in, its foldable pad. Each of the electrodes (410) is separated by approximately ½ inch and there is approximately 1 inch between the far right electrode and the right edge of its foldable pad. The foldable pads (320) are both covered with adhesive designed to adhere to patient skin. A removable liner sheet of non-stick material covers the foldable pad to preserve the adhesive so that it is fresh when applied to the patient's skin. This removable liner sheet measures approx. 4.75 inches by 5.5 inches. Each of the foldable pads (320) has a fold line at approximately 2.4 inches from the left edge. The resulting fold produces two 0.75 inch flaps that fold over either side of the pad. The completed/folded foldable pad is lightly tacked with glue to hold the folds together until pulled apart. When tabs are pulled, one with each hand, the folded pad first unfolds and the removable liner sheet is then removed in a single pulling action. The final folded pad measures 2.5 inches by 4.75 inches.

EXAMPLE

Embodiment 2

This embodiment starts with foldable pads (320) each measuring approximately 4.75 inches by 5.5 inches. Each of the foldable pads (320) has three electrodes with leads/wires exiting its foldable pad to attach to the automated external defibrillator (300). Each of the electrodes (410) measures approximately 1.25 inches by 4 inches and is adhered to its foldable pad. Each of the electrodes (410) is separated from another electrode by approximately 0.38 inches. There is approximately 1 inch between the far right electrode and the edge of its foldable pad. Each of the foldable pads (320) is covered with adhesive designed to adhere to patient skin. A removable liner sheet of non-stick material covers the foldable pad to preserve the adhesive so that it is fresh when applied to the patient's skin. This removable liner sheet measures approx. 4.75 inches by 5.5 inches. The edge of a liner is permanently affixed to left edge of the foldable pad. Each of the foldable pads (320) is folded into thirds using an accordion fold configuration: the left most 1.58 inches of each foldable pad is folded back, the next 1.58 inches is folded forward. The resulting folded configuration has two 0.75 inch flaps that fold over either side of the foldable pad. The completed/folded foldable pad is lightly tacked with glue to hold the folds together until pulled apart. When tabs are pulled, one with each hand, the folded pad first unfolds and the removable liner sheet is then removed from the paddle in a single pulling action. The final folded pad measures 1.58 inches by 4.75 inches.

Alternative embodiments of the device (200) may include limiting the use of the Smartphone (240) to audio/video, call and GPS functions such that the shock must be initiated by the button (230) on the case (205). Other embodiments could include LEDs (e.g., offline, charging, ready to shock indicators) into the device (200) as well as diagrams on the inside of the case that are visible when opened. Other embodiments may employ a button to shock, which would preferably be inside the case and viewable when the foldable pads (320) are unfolded for use. Other embodiments may include integral auto-injector technology, for example for emergency treatment for anaphylactic shock or management of diabetes. Such auto-injector technology would allow administration of a controlled/prescribed dosing into this device (200). Other embodiments would include a training module as part of the device (200).

The above-described embodiments including the drawings are examples of the invention and merely provide illustrations of the invention. Other embodiments will be obvious to those skilled in the art. Thus, the scope of the invention is determined by the appended claims and their legal equivalents rather than by the examples given.

INDUSTRIAL APPLICABILITY

The invention has application to the medical industry.

What is claimed is:

1. A method of making a device capable of administering an electrical shock to a patient and operable with a smartphone, the method comprising the steps of:
   providing a case;
   providing an automated external defibrillator fitting within the case;
   providing a case input/output port to the automated external defibrillator that mates with a corresponding smartphone input/output port;
   providing foldable pads fitting within the case, wherein each of the foldable pads comprises a plurality of electrodes that are electrically connectable to and detachable from the automated external defibrillator, wherein each of the foldable pads is unfoldable to expose a surface of each of the electrodes so that each said surface is movable for contacting with a patient's skin;
   providing a combined operating system for both the corresponding smartphone and the automated external defibrillator, said operating system auto loading and replacing the smartphone operating system upon starting the device after connection of the smartphone to the case input/output port;
   providing non-volatile memory connectable to the smartphone; and
   adding the combined operating system to the non-volatile memory.

2. The method of claim 1, further comprising the step of providing the smartphone.

3. A method of making a device capable of administering an electrical shock to a patient and operable with a smartphone, the method comprising the steps of:
   providing a case;
   enabling a smartphone, which is independent of the case, to be attached it to the case so as to provide necessary software to enable operability of the automated external defibrillator;
   providing an automated external defibrillator fitting within the case, said automated external defibrillator being inoperative without the addition of a smartphone;
   providing a case input/output port to the automated external defibrillator that mates with a corresponding smartphone input/output port; and
   providing foldable pads fitting within the case, wherein each of the foldable pads comprises one or more electrodes that are electrically connectable to and detachable from the automated external defibrillator, wherein each of the foldable pads is unfoldable to expose a surface of each of the electrodes so that each said surface is movable for contacting with a patient's skin.

\* \* \* \* \*